(12) United States Patent  
Grimm et al.

(10) Patent No.: US 11,845,921 B2  
(45) Date of Patent: Dec. 19, 2023

(54) DEVICE AND METHOD FOR EXAMINING A MEDIUM

(71) Applicant: Sartorius Stedim Biotech GmbH, Göttingen (DE)

(72) Inventors: Christian Grimm, Heiligenstadt (DE); Henry Weichert, Westewitz (DE); Mario Becker, Göttingen (DE)

(73) Assignee: Sartorius Stedim Biotech GmbH

( * ) Notice: Subject to any disclaimer, the term of this patent is extended or adjusted under 35 U.S.C. 154(b) by 0 days.

(21) Appl. No.: 16/770,049

(22) PCT Filed: Oct. 18, 2018

(86) PCT No.: PCT/EP2018/078624  
§ 371 (c)(1),  
(2) Date: Jun. 4, 2020

(87) PCT Pub. No.: WO2019/110185  
PCT Pub. Date: Jun. 13, 2019

(65) Prior Publication Data  
US 2020/0291344 A1    Sep. 17, 2020

(30) Foreign Application Priority Data  
Dec. 6, 2017   (DE) ...................... 10 2017 011 263.0

(51) Int. Cl.  
*C12M 1/26* (2006.01)  
*C12M 1/12* (2006.01)  
*C12M 1/34* (2006.01)

(52) U.S. Cl.  
CPC ............ *C12M 33/14* (2013.01); *C12M 37/02* (2013.01); *C12M 37/04* (2013.01); *C12M 41/32* (2013.01); *C12M 41/38* (2013.01); *C12M 41/46* (2013.01)

(58) Field of Classification Search  
CPC ...... C12M 33/14; C12M 37/02; C12M 37/04; C12M 41/32; C12M 41/38; C12M 41/41  
(Continued)

(56) References Cited

U.S. PATENT DOCUMENTS 4,700,560 A * 10/1987 Hoffa ................. G01N 33/0006  
                                          73/1.04  
5,800,692 A *  9/1998 Naylor ............. G01N 27/44743  
                                          204/451  
(Continued)

FOREIGN PATENT DOCUMENTS

DE    102006019242 A1    10/2007  
DE    102012003113 A1    8/2013  
(Continued)

OTHER PUBLICATIONS

International Search Report and Written Opinion for PCT/EP2018/078624, dated Feb. 4, 2019 (w/English International Search Report).  
(Continued)

*Primary Examiner* — Michael L Hobbs  
*Assistant Examiner* — Lenora A Abel  
(74) *Attorney, Agent, or Firm* — Klarquist Sparkman, LLP

(57) ABSTRACT

The invention relates to a device for examining a medium (100) inside a bioreactor (200; 201), comprising a sample-taking module (20) for taking a sample of the medium (100). The sample-taking module (20) comprises an uptake region (10; 10*a;* 10*b*) that can be arranged to make contact with the medium (100) inside the bioreactor (200; 201). At least two different membranes (15, 16) are positioned on the uptake region (10; 10*a;* 10*b*) of said sample-taking module (20), for the purpose of taking a sample of the medium (100).

13 Claims, 7 Drawing Sheets

Figure 1A:
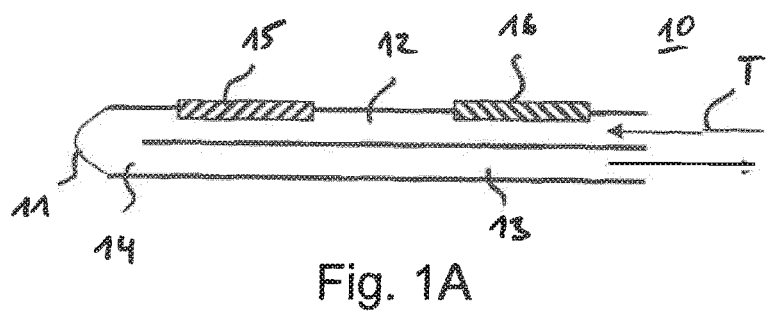

(58) Field of Classification Search
USPC .................................................... 435/297.1
See application file for complete search history.

(56) References Cited

U.S. PATENT DOCUMENTS

| | | | | |
|---|---|---|---|---|
| 6,692,968 | B2* | 2/2004 | Burshteyn | B01D 61/147 |
| | | | | 210/767 |
| 7,390,409 | B2* | 6/2008 | Demmer | B01D 15/22 |
| | | | | 210/198.2 |
| 9,017,997 | B2* | 4/2015 | Wuenn | C12M 29/10 |
| | | | | 435/297.1 |
| 2010/0113975 | A1* | 5/2010 | Kuennecke | B01D 61/243 |
| | | | | 600/573 |
| 2016/0201152 | A1* | 7/2016 | Medoff | C12P 19/02 |
| | | | | 127/55 |

FOREIGN PATENT DOCUMENTS

| | | |
|---|---|---|
| EP | 0448912 A2 | 10/1991 |
| EP | 1922987 A1 | 5/2008 |
| EP | 2405802 B1 | 12/2012 |
| WO | WO1996/030751 A | 10/1996 |
| WO | WO1996/033405 A1 | 10/1996 |
| WO | WO2009/120269 A2 | 10/2009 |

OTHER PUBLICATIONS

Office Action for German Application No. 10 2017 011 263, dated Aug. 9, 2018 (w/machine translation).
Office Action for European Application No. 18793622.4, dated Mar. 31, 2021 (w/English translation).

* cited by examiner

DEVICE AND METHOD FOR EXAMINING A MEDIUM

CROSS REFERENCE TO RELATED APPLICATIONS

This is the U.S. National Stage of International Application No. PCT/EP2018/078624, filed Oct. 18, 2018, which in turn claims the benefit of German Application No. 10 2017 011 263.0, filed Dec. 6, 2017, which application is incorporated herein in its entirety.

The invention relates to a device and a method for examining a medium inside a bioreactor, in particular a disposable bioreactor.

The trend in the biopharmaceutical industry is increasingly towards so-called disposable bioreactors, such as bags made of plastic film, which are also called bags. The expectation of end users of these disposable bioreactors is to have the same systems, measurement methods and parameters available as in classic stainless steel bioreactors. In particular, the measuring methods used should meet the same requirements as for stainless steel bioreactors in terms of their accuracy, reliability and the measuring range to be examined. To this end, various sensors, such as optical pH sensors and optical sensors for dissolved oxygen, are already integrated in the disposable bioreactors. This happens inter alia by welding special ports and special holding devices into the reactor wall of the disposable bioreactor.

A measurement of nutrients such as glucose or glutamine or metabolites such as lactate or glutamate is currently only possible by manual sampling and subsequent laboratory analysis or a stainless steel immersion probe. The immersion probes are designed in such a way that they can extract a continuous, representative amount of medium from the reactor through a membrane, by dialysis or filtration, and feed it to an analysis system.

A measurement of a target protein, e.g., a monoclonal antibody, is only possible by sampling, additional purification and subsequent laboratory analysis (HPLC or ELISA techniques).

The customary method for sterilizing disposable bioreactors is irradiation with up to 50 kGy gamma radiation. In order to keep disposable bioreactors sterile during sampling, it is necessary that an insertion of an immersion probe for continuous cell-free sampling be only possible via a special port, with particular attention to hygiene conditions. However, using such a probe can result in unwanted contamination of the cell culture process or damage to the disposable bioreactor.

Disposable bioreactors currently used are basically available in three main types. Stirred systems with impeller and sparger for gassing and agitation, shaken systems and systems realizing ventilation and mixing via wave movement, which are also referred to as RM for "rocking motion", In particular in current RM systems, it is not readily possible to insert stainless steel immersion probes due to the design of the disposable bioreactor and the movement which prevents permanent immersion of the immersion probes.

It is the object of the invention to improve the examination and/or purification of a medium inside a bioreactor, This object is solved by the subject matters of the independent claims. Preferred embodiments are the subject of the dependent claims.

One aspect relates to a device for examining a medium inside a bioreactor, in particular a disposable bioreactor, with a sampling module for taking a sample of the medium. The sampling module has an extraction region that can be arranged in touch-contact with the medium inside the bioreactor. At least two different membranes for taking a sample of the medium are arranged at the extraction region of the sampling module.

The device is designed and provided to examine online the medium arranged inside a bioreactor, i.e., essentially without disturbing and/or interrupting the biological process inside the bioreactor. Even if the device is designed to examine the contents of a disposable bioreactor, the device can also be designed to examine the contents of a stainless steel bioreactor and/or a pallet tank.

The sampling module can be designed as an immersion probe and/or can have an immersion probe, in particular an immersion probe made of stainless steel. The sampling module can also have a welding port and/or be designed as a welding port, in which the membrane(s) is/are arranged. Here, the welding port can be flat, e.g., have a bioreactor surface facing the interior of the bioreactor and/or an outer surface facing away from the interior of the bioreactor. Supply lines to the welding port can be arranged on a side of the sampling module facing away from the interior of the bioreactor, e.g., on the above-mentioned outer surface of the welding port. The sampling module can also have a hose and/or can be substantially hose-shaped. Here, at least one of the membranes can be designed as part of the hose wall. Furthermore, the sampling module can also have a tube and/or be essentially tubular.

The sampling module can also be used for the targeted purification of the medium of the bioreactor.

The extraction region of the sampling module can be designed and provided to be inserted into the interior of the bioreactor in an operating position. In the operating position of the device, the extraction region is arranged in touch-contact with the (e.g., biological) medium inside the bioreactor.

The extraction region can e.g., be designed as a probe part, which e.g., contains a probe tip. The extraction region can have a probe tip.

In the operating position, the extraction region can be guided into the interior of the bioreactor e.g., from the outside through a port in the reactor wall of the bioreactor.

The sampling module can have an external module region arranged outside the bioreactor in the operating position. The extraction region can be connected to the external module region via at least one transport line through the interior of the sampling module, in which a sample of the medium can be transported out of the bioreactor.

The sampling module can be designed to be secured to a holder on and/or relative to the bioreactor in such a way that the extraction region projects through the reactor wall into the interior of the bioreactor, while the external module region of the sampling module is arranged outside the bioreactor.

The extraction region can have a hollow inner region, into which the sample(s) of the medium can be introduced. The hollow inner region can be designed as part of the transport line.

The sampling module serves to take a sample of the medium from the interior of the bioreactor. Here, dialytic sampling can take place, wherein a sample is taken without reducing the total volume. The medium is usually a mixture of different extraction region such as cells, proteins, antibodies and/or smaller molecules such as e.g., glucose. Taking a sample here means that a sample is taken from at least one of these components of the medium, not necessarily a fraction of all different components of the medium. Here, tubular cleaning modules can be used, e.g., Filer devices.

The sample of the medium taken can be examined after sampling, e.g., after it has first been transported to the external module region of the sampling module and from there to an analysis module that does the actual analysis. The sampling module can e.g be connected and/or coupled to an external analysis system, e.g., to a mass spectrometer, a gas chromatograph, a liquid chromatography system such as an HPLC/UPLC system (which stands for High Performance Liquid Chromatography or Ultra Performance Liquid Chromatography) and/or an enzymatic analysis system such as Trace.

At least two different membranes for taking a sample of the medium are arranged at the extraction region of the sampling module. The two membranes can e.g., differ in which components of the medium can be taken as samples. The membranes can differ in particular in their cutoff pore size and/or can be designed to be differently permeable and/or to be of different strengths. The sampling module can in particular have exactly two different membranes for sampling. Alternatively, the sampling module can also have more than two different membranes.

As explained at the beginning, there have so far only been immersion probes for determining the concentration of nutrients. These have a specific membrane that is permeable to nutrients.

As to the examination of the medium, the invention is not limited to this one component of the medium, as in the case of a conventional immersion probe, but can extend the examination of the medium to several different components. This enables in particular the use of two different membranes for sampling.

This provides a new possibility to continuously take e.g., cell-free sample from a disposable bioreactor and feed it to an analyzer. This is e.g., also applicable to RM systems, i.e., bioreactors in which the disposable bioreactors are mixed using a rocking motion.

The device can also be used for purification, e.g., be designed as a tubular cleaning module.

With the device, it is possible to determine the concentration of nutrients and metabolites (such as glucose, lactate, glutamine, glutamate, biogenic amino acids, glycerol, acetate, ethanol or methanol) as well as target proteins (such as monoclonal antibodies, hormones, growth factors, interleukins, interferons) online in a disposable bioreactor at the same time.

In one embodiment, the device has only a single membrane, by means of which samples can be taken. Here, the membrane can be designed such that e.g., samples with at least two different particle diameters can be taken from the medium.

According to one embodiment, each of the at least two membranes is arranged on an outer region of the extraction region, so that each of the at least two membranes can be arranged in (direct) touch-contact with the medium inside the bioreactor. In this case, the two membranes can be in touch-contact with the medium in particular simultaneously, namely in the operating position of the device. In other words, the extraction region is delimited by two of the two membranes at two different points of its outer region, which is in touch-contact with the medium. Here, each of the membranes is arranged such that it allows in each case at least one component of the medium to pass through the membrane into the interior of the sampling module, e.g., in a transport line of the sampling module.

According to one embodiment, the at least two membranes differ at least in that they have differently sized cutoff pore sizes. The cutoff pore size can e.g., be expressed in kDa (kilodaltons) and determines a specific particle size. Components of the medium with a specific particle size smaller than the specific particle size determined by the cutoff pore size can diffuse through the respective membrane. If the particle size of the components deviates too much upward from the cutoff pore size, the particles cannot diffuse through the membrane, or only to a very limited extent.

According to a development of this embodiment, a first membrane of the at least two membranes has a cutoff pore size of 50 kDa to 200 kDa, and a second membrane of the at least two membranes has a cutoff pore size of 10 kDa to 30 kDa. The second membrane with the smaller cutoff pore size is particularly suitable for determining the concentration of smaller molecules such as nutrients (e.g., glucose or glutamine) and metabolites (e.g., lactate or glutamate), The first membrane with the larger cutoff pore size is particularly suitable for determining the concentration of larger molecules such as at least one predetermined target protein (e.g., an antibody).

According to one embodiment, a first membrane of the at least two membranes is designed and arranged to allow proteins to pass from the medium into the sampling module in touch-contact with the medium. A second membrane of the at least two membranes is designed and arranged to allow nutrients and/or metabolites to pass from the medium into the sampling module in touch-contact with the medium. For example, these can be membranes with the cutoff pore sizes mentioned above. When these membranes are used, two different components of the medium can be determined and/or examined with one device.

According to one embodiment, the sampling module has at least one transport line for transporting an adsorber through the extraction region along the transport line. Here, each of the at least two membranes limits the transport line to the outside. In other words, each of the two membranes is arranged between the transport lines and an outer region of the extraction region. The medium to be examined is also arranged in this operating region in the operating position. The outward limitation thus enables the membranes to come into direct touch-contact with the medium. The transport line is designed as a cavity in which the adsorber is guided. The adsorber is used to hold the samples, which in the operating position can diffuse through the respective membrane into the transport line to the adsorber. Different adsorbers can be provided for the different components. Different adsorbers can be transported through the one or more transport lines, which are each designed as adsorbers for the respective sample to be taken.

According to one embodiment, at least two different adsorbers are led through the transport line(s), which are each designed as adsorbers for the different components of the medium to be examined. Diffusion of the different components of the medium through the different membranes is triggered and/or supported with a respective adsorber specific therefor.

According to a further development of this embodiment, the device has a control module for controlling an adsorber flow through the at least one transport line of the sampling module. The control module can have a processor and/or be designed as a computer. The control module can in particular control one or more valves and/or pumps in such a way that the adsorber(s) is/are guided through the transport line at a predeterminable and/or variable speed. In this case, the adsorber(s) can be stopped, in particular, for a controllable and/or predeterminable time in order to enable enrichment with the components of the medium to be examined. Then the adsorber(s) enriched with the sample(s) can be carried on, in particular out of the extraction region and the sampling module to an analysis system or an analysis module.

According to an additional or alternative development of the embodiment, the sampling module has exactly one transport line through the extraction region, and the at least two membranes are arranged one behind the other in the transport direction through the transport line. In this case, two sections of the transport line that are offset from one another in the transport direction are enriched with the respective components of the medium to be examined before the adsorber(s) thus enriched is/are led out of the sampling module. Thus, only the formation of a single transport line is required in the extraction region, which enables a relatively simple and therefore inexpensive manufacture of the sampling module.

Alternatively, the sampling module has at least two transport lines through the extraction region, and the at least two membranes are arranged in different transport lines. Here, a separate transport line can be provided and designed for each component to be examined, and thus for each different membrane. Here, the control of the adsorber(s) can be made simpler, since only one enrichment has to take place in each transport line. Furthermore, only one type of adsorber has to be transported through each transport line. Furthermore, the individual components of the medium can be examined separately, e.g., in different analysis systems and/or different constituting parts of an analysis module.

According to one embodiment, the membranes are designed as dialysis membranes and/or semipermeable membranes. Such membranes are particularly suitable for bioreactors, since the device reduces the risk of contamination of the contents of the bioreactor.

According to one embodiment, the device has an analysis module for examining a sample of the medium taken by the sampling module. The analysis module is designed as a component of the device. The analysis module can be formed in several parts, in particular with at least two different measurement cells for examining at least two different components of the medium. The at least one sample can be supplied to the analysis module e.g., via a transport line, which is arranged running through the sampling module.

In a development of this embodiment, the analysis module is designed to determine a concentration of at least two different components in the medium by examining the sample of the medium taken. In particular, the two concentrations of the two different components that have diffused through the two different membranes can be determined. The device can be designed for online determination of the concentration of two different components of the medium. The different components of the medium can e.g., differ by their average molecular size.

One aspect relates to a method for examining a medium inside a bioreactor, in particular a disposable bioreactor, with the steps:
  arranging an extraction region of a sampling module in touch-contact with the medium inside the bioreactor;
  taking at least one sample of the medium through two different membranes of the sampling part;
  examining the sample of the medium taken.

The method can in particular be carried out with a device according to the aspect described above. For this reason, the statements made with regard to the device also relate to the method and vice versa, In particular when examining antibodies or target proteins using certain techniques such as MS or HPLC, it can be useful to increase the concentration of the antibodies even further. The concentration in the adsorber could be too low. Therefore, the method can e.g., be supplemented by a downstream chromatography, especially in the form of a capture step (e.g., Protein A Bind+Elute).

With the method, e.g., at least two samples of at least two different components of the medium can be taken. Alternatively, only a single sample can be taken, which is taken chronologically and/or spatially in succession on each of the at least two membranes. In other words, a sample of a first component can first be taken on a first membrane, then this sample can be supplemented on a second (different) membrane.

Here, the different components of the medium can diffuse through one of the two different membranes into the sampling module.

The method can be carried out online and be repeated (e.g., at regular intervals). With the method, e.g., the concentration of at least two different components of the medium in the bioreactor can be examined, determined and/or monitored.

In one embodiment, the two membranes are arranged in touch-contact with the medium in such a way that components of the medium pass through each of the two different membranes into at least one transport line through the extraction region of the sampling module. The at least one transport line runs at least through the extraction region of the sampling module and serves to receive and/or to transport the at least one sample.

In a development of the embodiment, an adsorber flow through the at least one transport line is controlled such that the components of the medium pass through each of the membranes into an adsorber resting in the transport line for a predeterminable period of time before the enriched adsorber is transported to an analysis module along the at least one transport line.

In one embodiment, the sample of the medium has at least two components that are extracted separately from one another through the two different membranes by an air bubble. In general, the components of the sample can be extracted spatially and/or temporally separated from one another through the two membranes. A first component of the sample taken through the first membrane may also be referred to as a first sample and/or first fraction and e.g., have at least a first type of sample particle. A second component of the sample taken through the second membrane may also be referred to as a second sample and/or second fraction and e.g., have at least a second type of sample particle. The two fractions are taken at least spatially separate from one another. The two fractions can e.g., be separated from each other by an air bubble. The air bubble can be generated by specifically controlling the fluids contained in the transport lines.

One aspect relates to the use of a device for examining a medium inside a bioreactor according to the above-described aspect for carrying out the method for examining a medium inside a bioreactor according to the further aspect described above.

In the context of this invention, the terms "substantially" and/or "approximately" can be used to include a deviation of up to 5% from a numerical value following the term, a deviation of up to 5° from a direction following the term and/or from an angle following the term.

Terms such as top, bottom, above, below, etc.—unless otherwise specified—refer to the Earth's reference system in an operating position of the subject matter of the invention.

Figure 1B:
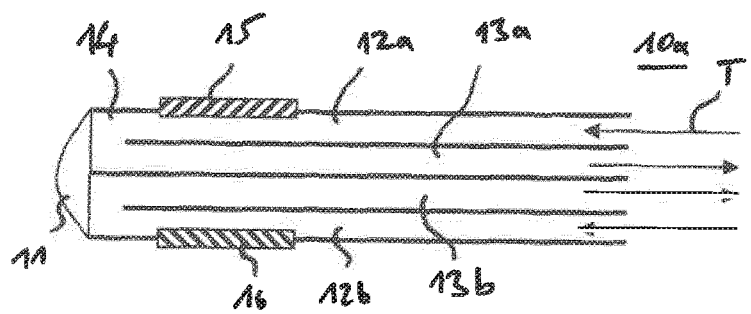
Figure 1C:
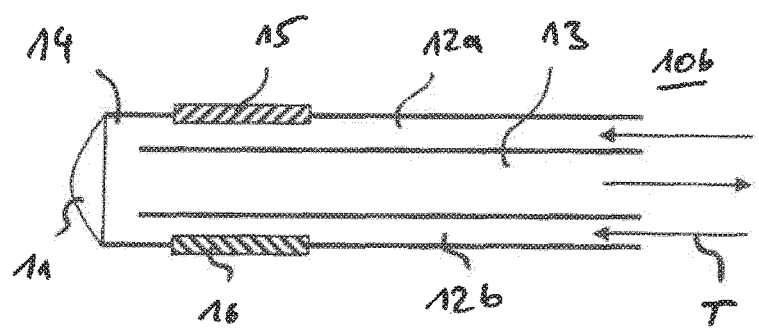
Figure 2:
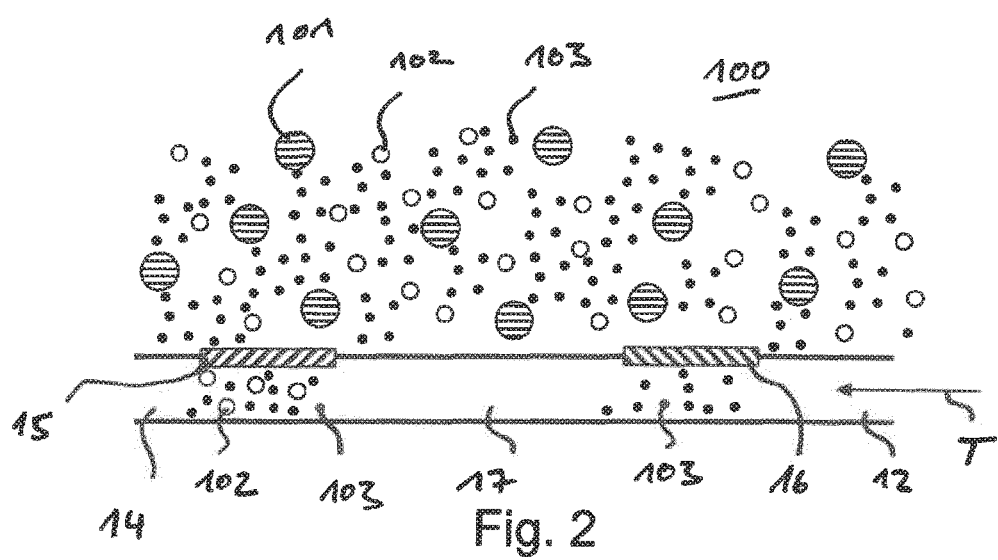
Figure 3:
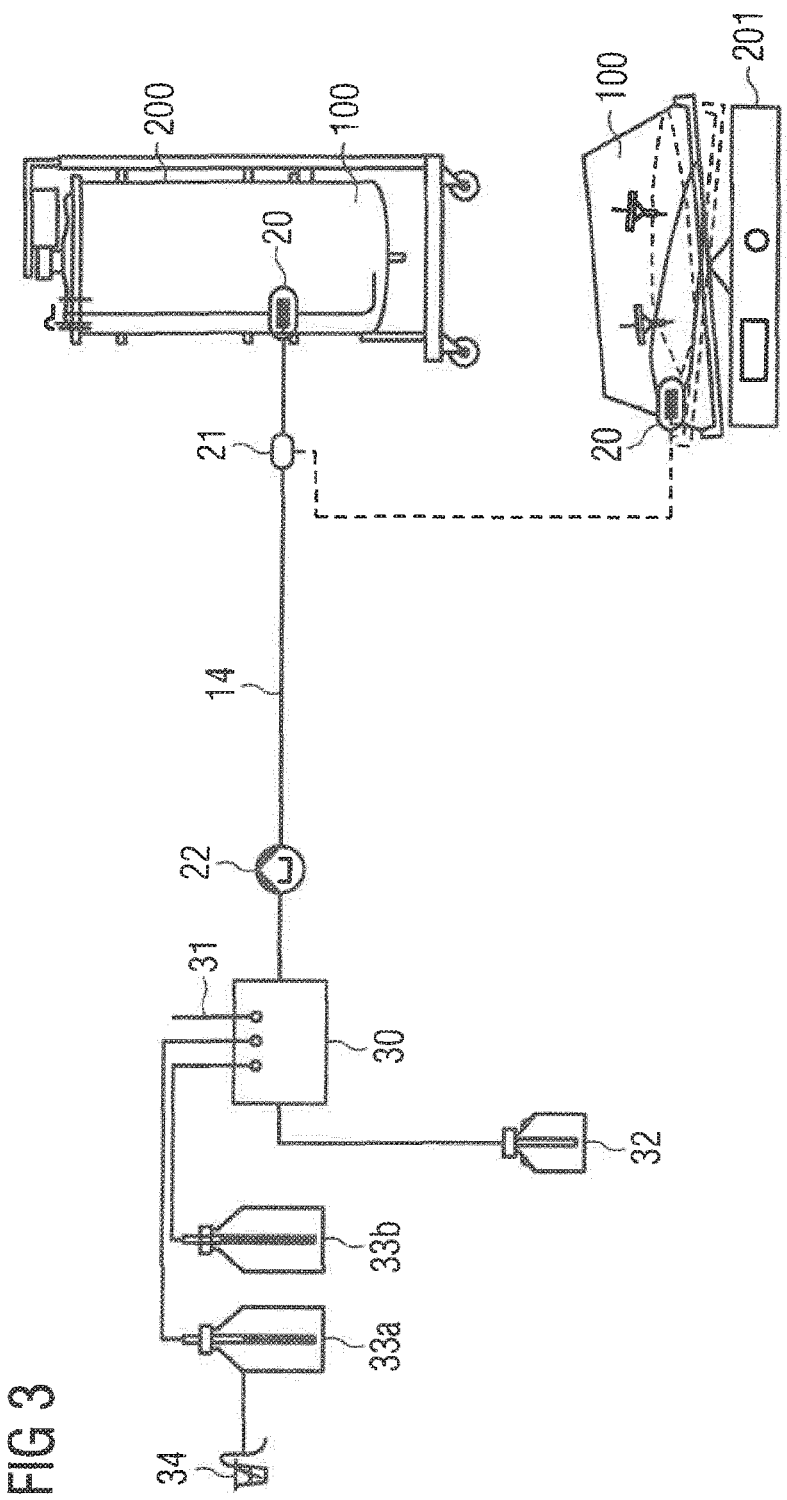
Figure 4:
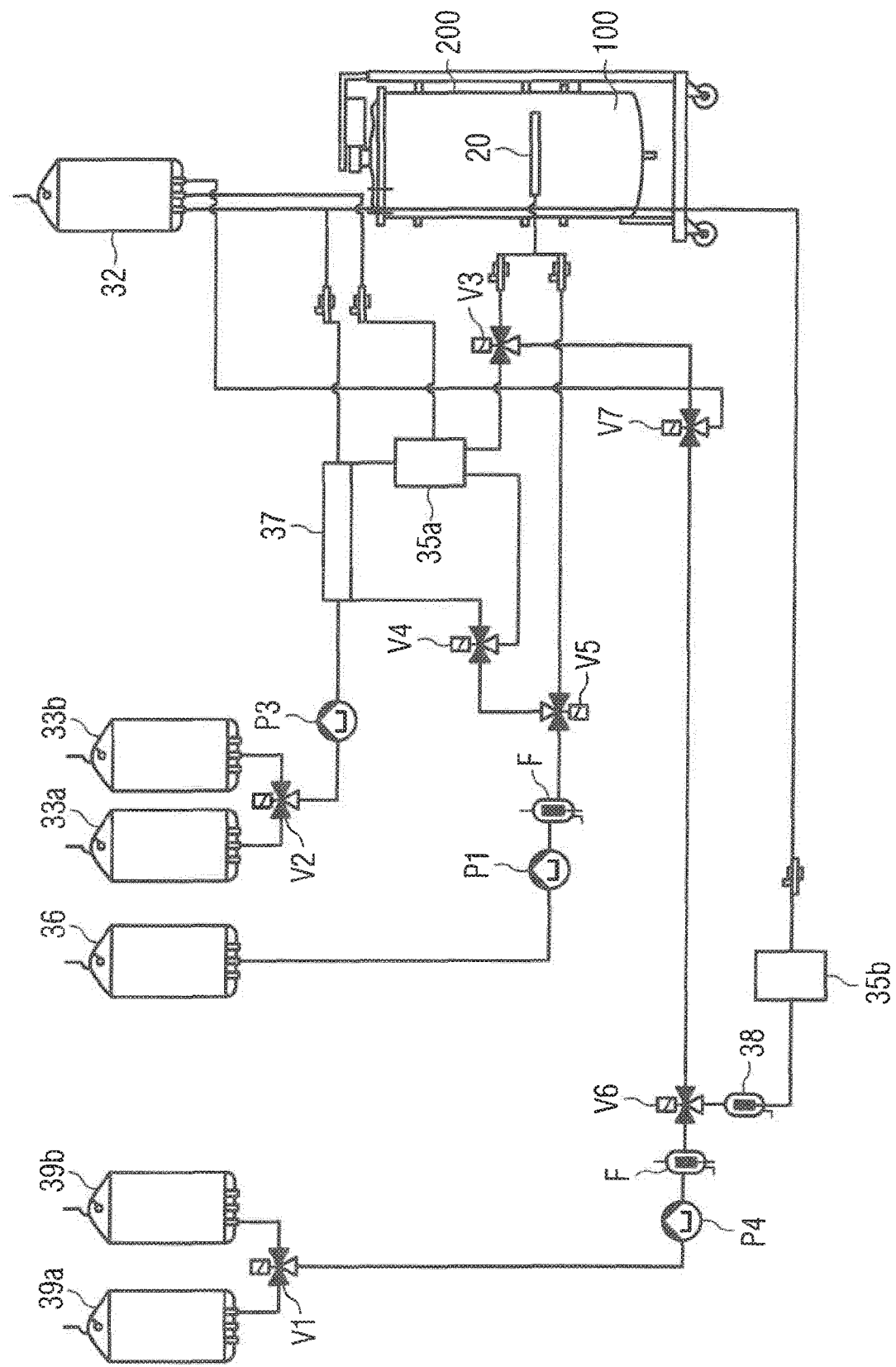
Figure 5:
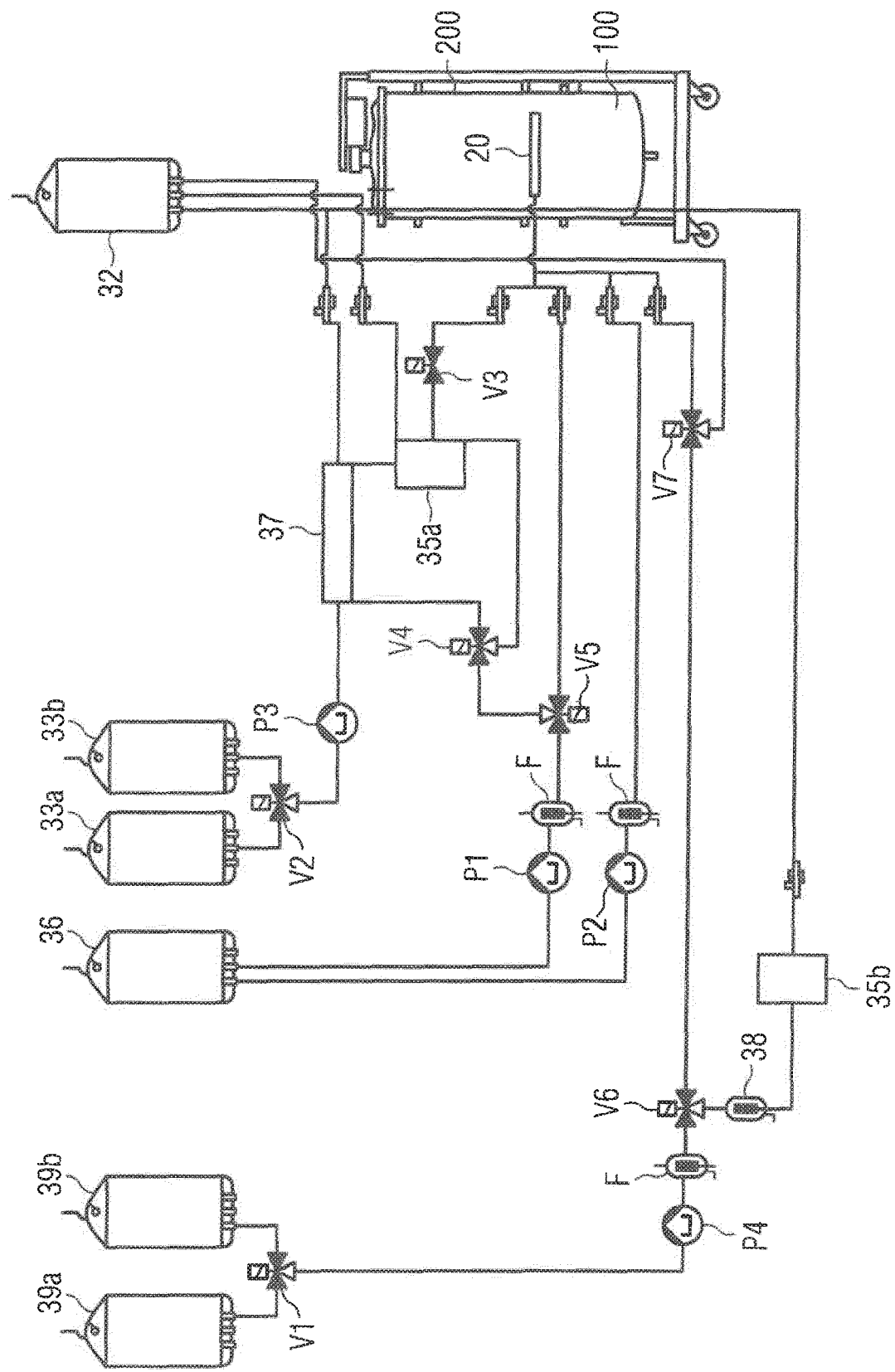
Figure 6:
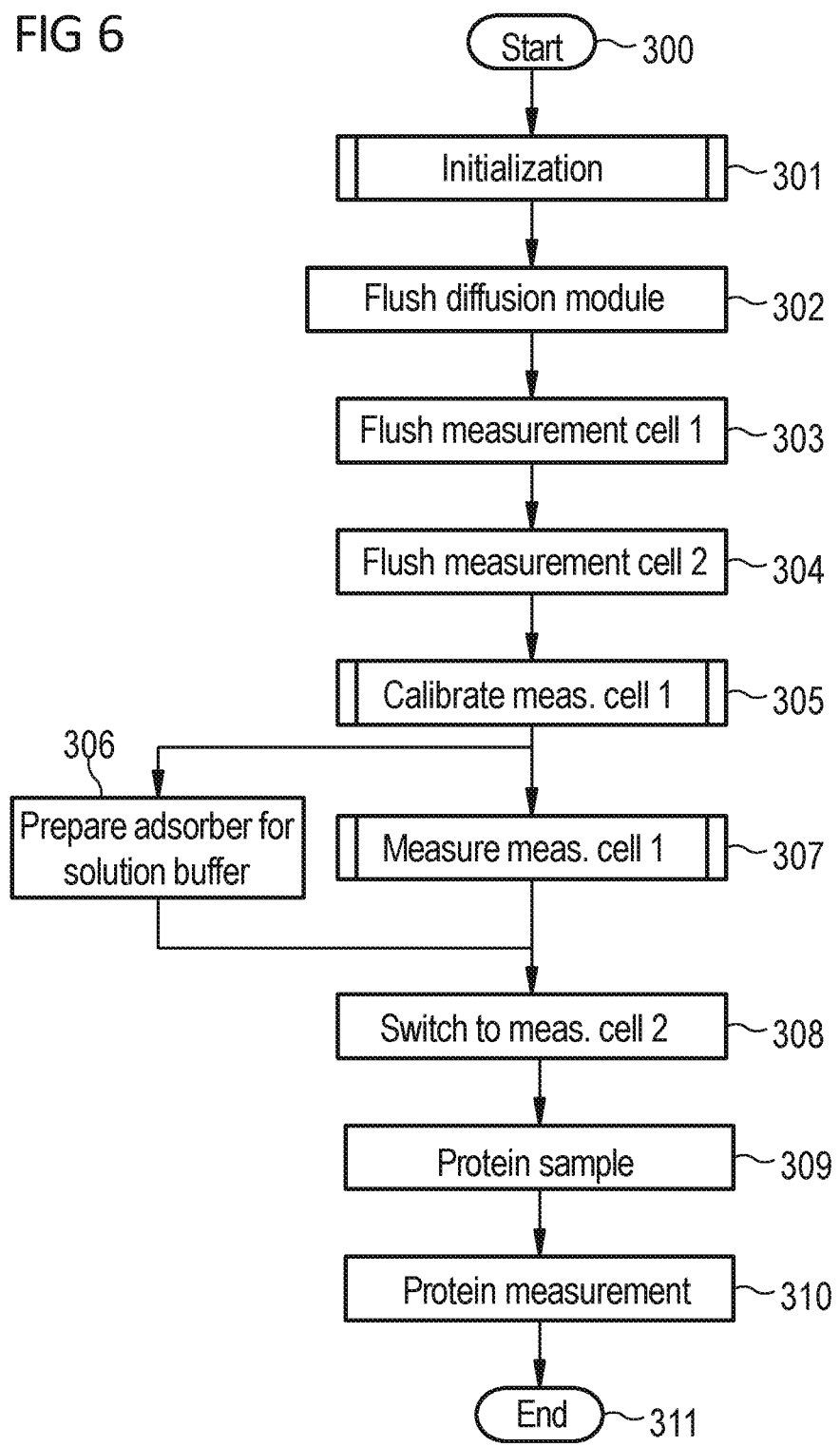
Figure 7:
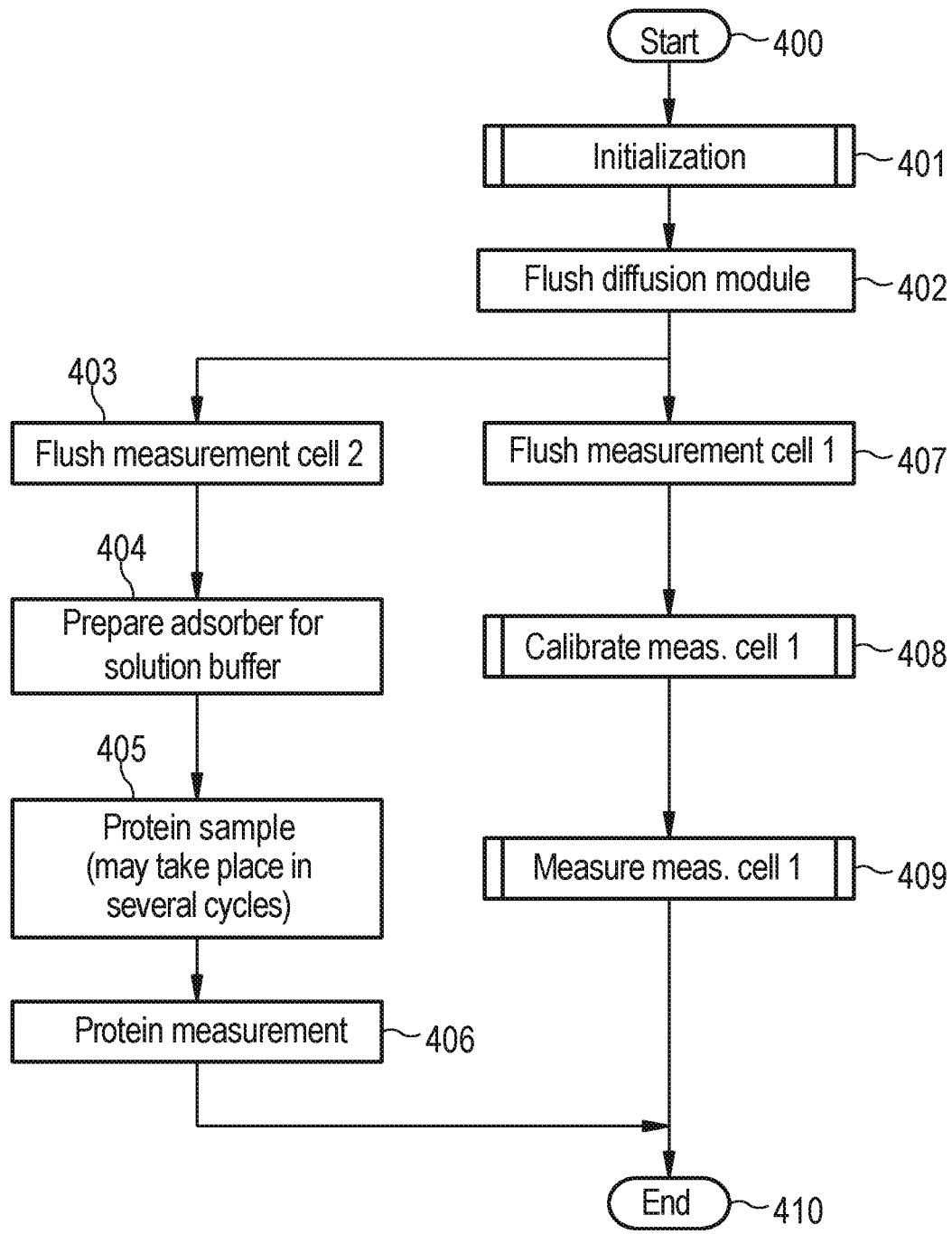

The invention will be described in more detail below with reference to embodiments shown in the figures. The same or similar reference numerals can designate the same or similar features of the embodiments. Individual features shown in the figures can be implemented in other exemplary embodiments. The figures show:

FIG. 1A a schematic representation of a first embodiment of an extraction region of a sampling module with a common transport line;

FIG. 1B a schematic representation of a second embodiment of an extraction region of a sampling module with two separate transport lines;

FIG. 1C a schematic representation of a third embodiment of an extraction region of a sampling module with a partly separate and partly common transport line;

FIG. 2 a schematic representation of the operating principle of the sampling;

FIG. 3 a schematic representation of a device for examining a medium inside a disposable bioreactor;

FIG. 4 a schematic representation of a device for examining a medium inside a disposable bioreactor with a serial sampling module;

FIG. 5 a schematic representation of a device for examining a medium inside a disposable bioreactor with a parallel sampling module;

FIG. 6 a schematic flow chart for controlling a device for examining a medium inside a disposable bioreactor with a serial sampling module; and FIG. 7 a schematic flow chart for controlling a device for examining a medium inside a disposable bioreactor with a parallel sampling module.

A device for examining a medium inside a bioreactor has at least one sampling module and can also have an analysis module.

A sampling module can have at least one pipeline as a transport line. The pipeline can be substantially U-shaped, terminated, fluid-transporting and/or made of plastic. In particular, the transport line can be formed in two parts such that two opposite transport directions are provided inside the transport line, i.e., for example a delivery and a removal line.

The sampling module has an extraction region that can be designed as a section of each pipeline in contact with the medium. The extraction region is designed and provided to be inserted into the interior of the bioreactor through the reactor wall of the bioreactor in such a way that the extraction region is in direct touch-contact with the medium.

FIG. 1A shows a schematic representation of a first embodiment of an extraction region 10 of a sampling module with a common transport line 14.

At least one membrane, in particular a dialysis membrane, is arranged in the extraction region 10. In the embodiment shown, the extraction region 10 has a first membrane 15 and a second membrane 16, which are arranged in series in the transport direction T. The membranes 15 and 16 are each arranged in a recess in an outer wall of the transport line 14 in such a way that they at least partially seal the transport line 14 at this recess. At the respective recess, the respective membrane 15, 16 replaces the recessed line wall of the transport line 14. Since the membranes 15 and 16 are at least partially permeable to predetermined components of the medium, the seal is not completely but only partially formed.

The transport direction T is marked with arrows in the figures and follows the course of the common transport line 14 through the extraction region 10. The transport direction T runs through a common detection channel 12 (as a delivery line) of the transport line 14 to a probe tip 11, at which the common detection channel 12 terminates. On the probe tip 11, the transport line 14 is substantially U-shaped, which is why the transport direction T is reversed here by approximately 180°. In other words, the transport direction T reverses at the probe tip 11.

After this turn at the probe tip 11, the transport direction T runs from the probe tip 11 along a common removal channel 13. The common detection channel 12 is arranged substantially parallel to the common removal channel 13, the directions of transport T through these two channels 12 and 13 to one another essentially being opposite.

The inlet and outlet of the transport line 14 can be terminated with a pipe connection element at the probe tip 11.

Different membranes are combined with one another in the transport line 14, namely the first membrane 15 and the second membrane 16. These membranes 15, 16 can be designed as semipermeable membranes and/or dialysis membranes. The two membranes 15, 16 can have different properties, in particular different cutoff pore sizes. For this reason, the two membranes 15, 16 hold back and/or allow different components of a medium of a bioreactor to pass through. For example, the second membrane 16 can e.g., have a cutoff pore size of about 10 kDa to about 30 kDa, which only allows smaller molecules such as nutrients (e.g., glucose) and metabolites (e.g., lactate) to pass through the second membrane 16. The first membrane 15 can e.g., have a cutoff pore size of about 50 kDa to about 200 kDa, which allows larger components (e.g., a target protein such as an antibody of the medium) to pass through the first membrane 15.

An advantage of the two membranes connected in series can be that in a first fraction, which is assigned to the first membrane, a substantially protein-free sample for e.g., a nutrient and/or metabolite analysis may be included. This first fraction can be spatially and/or temporally from a second fraction assigned to the second membrane. In the second fraction, e.g., a protein and various other components such as nutrients, metabolites etc. may be present. It can happen that any existing nutrients do not interfere with the analysis and/or purification of the proteins. With the first fraction, the proteins and antibodies would be quite disturbing for e.g., an enzymatic analysis. The first and second fractions can correspond to first and second samples, respectively, which can be extracted through the respective membrane.

In one embodiment, the second membrane can be formed as a 10 kDa Hydrosart membrane, e.g., the Sartorius type: 14439. In this or another embodiment, the first membrane can be designed as a 100 kDa Hydrosart membrane, e.g., the Sartorius type: 14468.

Alternatively, another material can be used, so that instead of the Hydrosart (a cross-linked cellulose) e.g., polyethersulfone can be used, corresponding to Sartorius types 14639 and 14668.

Furthermore,
the Ultracel series (RC membrane from Millipore, cellulose based) and/or
the omega series (PES UF from Pall) and/or
hollow fibers, e.g., made of polysulfone from spectrum can also be used as membranes.

Through the two membranes 15 and 16, different components of the medium can pass into the same, common transport channel 14 at positions offset serially one behind the other along the transport channel 14. One or more adsorber solution(s) can be provided in the transport channel 14 as a means of transport. The adsorber solution can be designed and/or provided for receiving the components of the medium in the transport channel 14 and for transporting the components received along the transport channel 14. The different components of the medium, which pass through the two different membranes 15, 16 into the same transport channel 14, can be transported along the same, common transport channel 14 past the probe tip 11 out of the extraction region 10 and the bioreactor.

FIG. 1B shows a schematic representation of a second embodiment of an extraction region 10a of a sampling module with two separate transport lines 14. Overall, the second embodiment is similar to the first embodiment, which is why similar and/or the same features of the embodiments are designated with the same reference numerals.

In contrast to the first embodiment, the extraction region 10a shown in FIG. 1B has two separate transport lines 14. A first one of these separate transport lines 14 has a first detection channel 12a, which is deflected at the probe tip 11 to a first removal channel 13a. The first membrane 15 is integrated in an outer wall of the first detection channel 12a. First components of the medium can pass through the first membrane 15 into the first detection channel 12a and can be transported out of the extraction region 10a and out of the sampling module through the first removal channel 13a.

A second one of the separate transport lines 14 has a second detection channel 12b, which is deflected at the probe tip 11 to a second removal channel 13b. The second membrane 16 is integrated in an outer wall of the second detection channel 12b. Second components of the medium can pass through the second membrane 16 into the second detection channel 12b and can be transported out of the extraction region 10a and out of the sampling module through the second removal channel 13b separately from the first components.

FIG. 1C shows a schematic representation of a third embodiment of an extraction region 10b of a sampling module with partly separate transport lines 14 and partly common transport lines 14. Overall, the third embodiment is similar to the first and second embodiments, which is why similar and/or the same features of the embodiments are designated with the same reference numerals.

In contrast to the second embodiment, the extraction region 10b shown in FIG. 1C has two transport lines 14 which are only partially separated from one another. A first detection channel 12a is deflected at the probe tip 11 to a common removal channel 13. The first membrane 15 is integrated in an outer wall of the first detection channel 12a. First components of the medium can pass through the first membrane 15 into the first detection channel 12a and can be transported out of the extraction region 10b and out of the sampling module through the common removal channel 13.

A second detection channel 12b is likewise deflected at the probe tip 11 to the common removal channel 13. The second membrane 16 is integrated in an outer wall of the second detection channel 12b. Second components of the medium can pass through the second membrane 16 into the second detection channel 12b and (together with the first components) can be transported out of the extraction region 10b and out of the sampling module through the removal channel 13.

The embodiments shown in FIGS. 1A, 1B and 1C can be controlled with the transport direction T reversed.

Different adsorber liquids for adsorbing and/or transporting the different components of the medium can be guided in the separate detection channels 12a and 12b.

In other embodiments not shown in the figures the transport lines can also be designed differently and/or more than two different membranes can be used, e.g., three membranes for examining at least three different components of the medium.

The membranes 15 and/or 16 can be fastened to the transport line 14 by means of different joining techniques, which line can e.g., can be formed from plastic. For example, as a technique "heat sealing" can be used, i.e., thermal welding of the membrane to the plastic carrier. In the case of a cellulose-based membrane, for example, this joining technique can be disadvantageous, since this material cannot be easily welded to another plastic. In this case, i.e., when a cellulose-based membrane is used, the following alternatives can be used:

a) Gluing: The membrane can be glued with a special adhesive. Due to possible problems with extractables/leachables, this alternative is rather unfavorable in the biotech sector.

b) Clamping: The membrane can be clamped and/or pressed between plastic parts, e.g., also using elastomer seals in between.

c) Overcasting: Here, parts of the membrane are covered with a thermoset/elastomer (e.g., silicone) for fixing and sealing.

d) Overmolding: recasting and/or overmolding of the membrane with a thermoplastic.

These joining techniques can also be used with other membranes.

FIG. 2 shows a schematic representation of the operating principle of the sampling. Here, emphasis is placed on particular on the sampling by means of a sampling module that has the first extraction region 10 shown in FIG. 1A with the membranes 15, 16 arranged in series one behind the other. The first extraction region 10 is only partially shown, in particular without the probe tip 11 and without the removal channel 13.

The upper half of FIG. 2 shows a medium 100 that has several components. Three different components of the medium 100 are represented by different symbols. The medium thus has a plurality of cells 101, which are shown as large, cross-striped circles. Furthermore, the medium 100 has a plurality of proteins and/or antibodies 102, which are shown as empty, medium-sized circles. Finally, the medium 100 has a plurality of smaller molecules 103, which are shown as small dots. The smaller molecules 103 can e.g., be formed as glucose and/or lactate. The cells 101, the proteins 102 and the smaller molecules 103, mixed together as a medium 100, are arranged inside a bioreactor (not shown).

The extraction region 10 of a sampling module, which is partially shown in FIG. 2, is introduced into the interior of the bioreactor. The extraction region 10 is arranged inside the bioreactor in such a way that at least the two membranes 15 and 16 are arranged in direct touch-contact with the medium 100. Here, the first membrane 15 is at least partially arranged as a border region between the medium 100 and the interior of the detection channel 12. At another location on the transport line 14, the second membrane 16 is at least partially arranged as a border region between the medium 100 and the interior of the detection channel 12. An intermediate region 17 is formed in the interior of the transport line 14 between the two membranes 15 and 16. In the transport direction T through the detection channel 12, first the second membrane 16 is arranged, which adjoins the intermediate region 17, which in turn adjoins the first membrane 15.

In the embodiment shown, the second membrane 16 has a smaller cutoff pore size than the first membrane 15, e.g., from 10 kDa to 30 kDa, preferably from 10 kDa to 20 kDa. For this reason, only the smaller molecules 103 can pass through and/or diffuse through the second membrane 16 into the transport line 14. A second diffusion time granted for this can be predetermined and/or adjustable and/or controllable and/or regulatable. During the second diffusion time, an adsorber located in the transport line 14 may not be driven, but rather left to rest in order to give the smaller molecules 102 time to pass into the transport channel 14. The adsorber can then be driven a little further, e.g., up to the first membrane 15.

The first membrane 15 has a larger cutoff pore size than the second membrane 16, e.g., from 50 kDa to 200 kDa, preferably from 75 kDa to 125 kDa. For this reason, the medium-sized components of the medium 100 can diffuse through the first membrane 16, in particular the proteins and/or antibodies 101. A first diffusion time granted for this can be predetermined and/or adjustable and/or controllable and/or regulatable. During the first diffusion time, the adsorber located in the transport line 14 may not be driven, but can be left to rest in order to give the medium-sized molecules 102 time to pass into the transport channel 14. The adsorber can then be driven further. In order to transport all samples of the medium out of the sampling module and to analyze them in an analysis system and/or an analysis module.

The adsorber can be controlled via an external drive. In particular, a region with little and/or no concentration can be formed in the intermediate region 17, e.g., an air bubble as a separating agent between the two detection regions inside the transport line 14.

Alternatively, the adsorber may not be stopped at the first and/or second diffusion time, but can be guided through the transport line 14 substantially at a constant speed.

By sampling shown schematically in FIG. 2, samples of two different components of the medium 100 can be taken. These samples can be analyzed in an external analysis system and/or an external analysis module. For example, the concentration of the two components in the medium 100 can be detected and/or determined in this way.

FIG. 3 shows a schematic representation of a device for examining a medium inside a bioreactor 200 and/or an RM bioreactor 201. The bioreactor 200 can be arranged in a tank, e.g., a stainless steel tank. The bioreactor itself can be designed as a disposable bioreactor, e.g., as a plastic bag filled with the medium 100, which is arranged in the tank shown. The bioreactor 200 can be mixed e.g., by means of a stirring mechanism. The stirring mechanism may have a driven axle that projects into the bioreactor 200. The stirring mechanism can also drive the medium 100 by means of rocking motion (abbreviated as RM), that is to say mix it by means of a rocking motion. Such an RM bioreactor 201 is shown schematically in FIG. 3 below.

The device has a sampling module 20. The sampling module 20 has at least one extraction region, e.g., the extraction region 10, 10a and/or 10b shown in FIGS. 1A, 1B and 1C.

The sampling module 20 is arranged such that it at least partially penetrates the reactor wall of the bioreactor 200 and/or 201. In an operating position, the extraction region 10 of the sampling module 20 can in particular be arranged completely inside the bioreactor 200 and/or 201. Here, in particular, the two membranes 15 and 16 are in direct touch-contact with the medium 100.

The transport line 14 through the extraction region 10 leads into and out of the sampling module 20 and out to an analysis module 30 of the device for examining the medium 100. A sterile connection 21 can optionally be formed in this transport line 14 arranged externally from the sampling module 20. Furthermore, a pump 22 can be arranged between the analysis module 30 and the sampling module 20, e.g., a persistaltic pump for driving a content of the transport line 14 (e.g., an adsorber).

The basic structure of an analysis system for measuring nutrients in a bioreactor is already known. In the analysis module shown, however, besides the measurements of the nutrients (such as glucose, lactate, etc., i.e., the smaller molecules 103), a measurement of the content of target proteins 102 can also be carried out.

The analysis module 30 can have at least one measurement cell and at least one analyte sensor 31 in order to determine the concentration of at least two components of the medium 100. Sample residues that have already been examined and/or are not required can be disposed of in a waste container 32. For this purpose, the analysis module 30 can be connected to the waste container 32 via a waste line.

Furthermore, the analysis module 30 can be connected to a first calibration solution 33a and a second calibration solution 33b, which are designed to calibrate the analysis module 30. An inspection device 34 can be used to inspect the calibration solutions 33a and 33b.

FIG. 4 shows a schematic representation of a device for examining a medium 100 inside a bioreactor 200 with a serial sampling module 20 with more details than FIG. 3. In particular, additional components and/or features of the analysis module 30 are shown in FIG. 4. The serial sampling module 20 may have the extraction region 10 shown in FIG. 1A, in which the membranes 15 and 16 are arranged in series one behind the other.

A transport solution 36 from a tank serves to pass through the transport line 14. The transport solution 36 can contain a buffer and/or adsorber for receiving predetermined components of the medium 100. The transport solution 36 is connected to a left inlet of a fifth valve V5 via a first measuring pump P1 and a filter F. A right inlet of the valve V5 is connected to the sampling module 20, e.g., via the transport line 14.

A partial outlet of the fifth valve V5 is connected to a left inlet of a fourth valve V4. A right inlet of the fourth valve V4 is connected to a diffusion module 37. A partial outlet of the fourth valve V4 is connected to a first measurement cell 35a. Moreover, the diffusion module 37 is connected directly to the first measurement cell 35a.

The first measurement cell 35a is connected to a left inlet of a third valve V3. A right inlet of the third valve V3 is connected to the sampling module 20, e.g., via a channel of the transport line 14. Furthermore, the first measurement cell 35a is connected to a waste container 32, just like the diffusion module 37.

A first calibration solution 33a is connected to a left inlet of a second valve V2. A second calibration solution 33b is connected to a right inlet of the second valve V2. A partial outlet of the second valve V2 is connected to the diffusion module 37 via a third pump P3, which can be designed as a sampler pump.

A binding buffer 39a is connected to a left inlet of a first valve V1. A solution buffer 39b is connected to a right inlet of the first valve V1. A partial outlet of the first valve V1 is connected to a left inlet of a sixth valve V6 via a fourth pump P4, which can be designed as an adsorber pump, and via a filter F.

A right inlet of the sixth valve V6 is connected to a left inlet of a seventh valve V7. A partial outlet of the seventh valve V7 is connected to the waste container 32. A right inlet of the seventh valve V7 is connected to the partial outlet of the third valve V3.

A partial outlet of the sixth valve V6 is connected to a second measurement cell 35b via a membrane adsorber 38, said second measurement cell 35b being also connected to the waste container 32.

FIG. 5 shows a schematic illustration of a device for examining a medium 100 inside a bioreactor 200 with a parallel sampling module 20. The parallel sampling module 20 can e.g., have the extraction region 10a shown in FIG. 1B, in which the membranes 15 and 16 are arranged parallel to one another in two separate transport lines 14. FIG. 5 shows additional components and/or features of the analysis module 30 of FIG. 3.

The device shown in FIG. 5 is largely identical to the device shown in FIG. 4. In contrast to the device shown in FIG. 4, the transport solution 36 is guided through two separate transport lines 14. For this reason, the container and/or tank with the transport solution 36 is additionally connected to the sampling module 20, more precisely to the second transport line 14 through the extraction region 10a, via a second pump P2, which can be designed as a measuring pump, via a filter F. Here, the transport solution 36 is preferably connected to the first or second detection channel 12a or 12b. The associated first or second discharge channel 13a or 13b is connected to the right inlet of the seventh valve V7 (and above that to the second measurement cell 35b).

The right inlet of the fifth valve V5 is directly connected to the other detection channel 12a or 12b, and the partial outlet of the third valve V3 is closed.

The transport solution 36 can be passed as a buffer from the associated transport buffer container through the second transport line 14 with the membrane, which is permeable to the target protein 102 (the first membrane 15 in the exemplary embodiments shown). The transport solution 36, which is then enriched with protein 102, is passed through the seventh valve V7 and the sixth valve V6 onto the protein A membrane adsorber 38. Specific binding of protein A to the Fc part of the antibodies can lead to selective concentration. After a certain time, which can correspond to a certain sample volume, the valve is then switched and an eluate buffer (from the solution buffer 39b) then releases the bound antibody from the protein A membrane adsorber 38 again. This eluted antibody is then detected in the second measurement cell 35b. This measurement cell 35b can be designed as an optical measurement cell, which can be used e.g., for absorption, emission or scatter measurements such as UV/VIS, fluorescence, NIR, MIR, RAMAN, etc. The detection can e.g., be via the absorption in the UV range at 280 nm. In addition, an eluted antibody can be added for special analyzes (e.g., biological automated assays—binding tests, methods such as MS, HPLC etc.). The adsorber is then regenerated again with the binding buffer 39a and the cycle can begin again.

The method described for the protein A membrane adsorber 38 can also be applied to other modifications of the membrane adsorber 38, these can be other protein modifications (e.g., protein G, antibody-specific binding structures, receptor proteins) or other chemical modifications of the membrane adsorber (e.g., ion exchange chromatography or hydrophobic interaction). The method step with protein A is optional and can also be omitted. In one embodiment, this can also be measured directly.

FIG. 6 shows a schematic flow diagram for controlling a device for examining a medium inside a disposable bioreactor with a serial sampling module 20, i.e., the device shown in FIG. 4, for example.

The method is first started in method step 300.

During the subsequent initialization in method step 301, the components and/or modules of the device can be set to their starting conditions and/or it can be checked whether the components and/or modules of the device are already set to their respective starting conditions. In particular, the starting conditions of the pumps P1, P3, P4 and/or valves V1 to V7 can be set and/or checked.

In the device shown in FIG. 4, the following starting conditions are set in method step 301: the first, second and third valves V1, V2 and V3 are closed. The fourth and seventh valves V4 and V7 are open from inlet to inlet. The fifth valve V5 is open between the partial outlet and the left inlet. The sixth valve V6 is open between the partial outlet and the right inlet. All pumps P1, P3 and P4 are off.

The diffusion module 37 is then flushed in method step 302. To do this, the first measuring pump P1 is switched on. The fourth and fifth valves V4 and V5 were already set during the initialization in such a way that the transport solution 36 now flushes through the diffusion module 37 and, if necessary, flushes any residues into the waste container 32.

The first measurement cell 35a is then flushed in method step 303. For this purpose, the fourth valve V4 is opened between the partial outlet and the left inlet. Then (with the first measuring pump P1 still working) the transport solution 36 can be flushed through the first measurement cell 35a, with any residues that may be present being flushed into the waste container 32.

The second measurement cell 35b is then flushed in method step 304. For this purpose, the fifth valve V5 is opened from inlet to inlet and the third valve V3 is opened between the partial outlet and the right inlet. Then (with the first measuring pump P1 still working) the transport solution 36 can be flushed through the valves V5, V7 and V6 through the second measurement cell 35b, with any residues that may be present being flushed into the waste container 32.

The first measurement cell 35a is then calibrated in method step 305. For this purpose, the first measuring pump P1 is first switched on, the fifth valve V5 is opened from the partial outlet to the left inlet, the fourth valve V4 is opened from the inlet to the inlet and the second valve V2 is opened from the partial outlet to the left inlet. A calibration measurement of the first calibration solution 33a in the first measurement cell 35a is carried out. Then the second valve V2 is closed and the sample pump P3 is switched off.

Then one waits for a short time.

Then, the second valve V2 is opened from the partial outlet to the right inlet and the sample pump P3 is switched on. Now, the first calibration solution 33a can be pumped to the diffusion module 37 and/or the first measurement cell 35a. A further calibration measurement of the first calibration solution 33a is carried out in the first measurement cell 35a. Then, the second valve V2 is closed and the sample pump P3 is switched off.

The following method steps 307 and 306 can take place in parallel or alternatively to one another.

In method step 306, the adsorber for the solution buffer 39a is prepared. For this purpose, the sixth and first valves V6 and V1 are opened from the partial outlet to the left inlet and the adsorber pump P4 is turned on. Now, the solution buffer 39a is pumped through the second measurement cell 35b.

In method step 307, a measurement is carried out on the first measurement cell 35a. For this purpose, the fifth valve V5 is opened from inlet to inlet, the fourth valve V4 is closed, the third valve V3 is opened from inlet to inlet, and the first pump P1 is switched off.

Then one can wait e.g., for a predetermined diffusion period until components (e.g., the smaller molecules 103) of the medium 100 as the first sample have diffused through one of the two membranes 15 and 16 (in the exemplary embodiment shown in FIG. 2 through the second membrane 16).

Then the first measuring pump P1 is switched on until the first sample thus taken is transported into the first measurement cell 35a. A measurement takes place in the first measurement cell 35a, in particular a determination of the concentration of the respective components of the medium 100 to be examined.

The first measuring pump P1 is then switched off again.

After the two method steps 306 and 307, a switch is made to the second measurement cell 35b in method step 308. For this purpose, the third valve V3 is opened from the partial outlet to the right inlet, so that solution buffers 39a reach the sampling module 20 through the sixth and seventh valves V6 and V7.

In method step 309, a sample of the target protein 102 is taken in the sampling module. For this purpose, the fourth pump P4 is switched off, the sixth valve V6 is opened from the partial outlet to the right inlet, the first valve V1 is closed, and the first measuring pump P1 is switched on. Then one can wait e.g., for a predetermined diffusion period until components (in particular proteins 102) of the medium 100 as a second sample have diffused through one of the two membranes 15 and 16 (in the exemplary embodiment shown in FIG. 2 through the first membrane 15).

In method step 310, a protein measurement is carried out on the second measurement cell 35b. Then, the first measuring pump P1 is switched off (alternatively, the third valve V3 can also be opened from inlet to inlet for a further measurement on the first measurement cell 35a in method step 307).

This is followed by flushing, the sixth valve V6 being opened from the inlet to the inlet, the seventh valve V7 being opened from the partial outlet to the left inlet, the first valve V1 being opened from the partial outlet to the right inlet, and the fourth pump P4 being switched on. The solution buffer 39b now displaces the binding buffer 39a. Both dilution and measurement take place in the second measurement cell 35b, the sixth valve V6 being opened from the partial outlet to the left inlet. The binding buffer 39a transports the antibody to the membrane adsorber and at the same time ensures good binding of the antibody to the protein of the adsorber, which e.g., can also be a classic prot. A pillar. This can also be done in several cycles until the adsorber is sufficiently loaded. Then, the solution buffer 39b, which can be designed as an elute buffer, ensures that the antibody is removed from the protein A again and the highly concentrated antibody solution is transported into the measurement cell. In the measurement in the second measurement cell 35b, in particular a concentration determination of the respective components of the medium 100 to be examined (here: the target protein 102) can take place.

The method terminates with the last method step 311. Alternatively, the method can also be carried out iteratively, that is, instead, it can be continued again with method step 300 or 301, etc.

FIG. 7 shows a schematic flow diagram for controlling a device for examining a medium inside a disposable bioreactor with a parallel sampling module 20, i.e., the device shown in FIG. 5, for example.

The method is first started in method step 400.

During the subsequent initialization in method step 401, the components and/or modules of the device can be set to their starting conditions and/or it can be checked whether the components and/or modules of the device are already set to their respective starting conditions. In particular, the starting conditions of the pumps P1 to P4 and/or valves V1 to V7 can be set and/or checked.

In the device shown in FIG. 5, the following starting conditions are set in method step 401: The first, second, third and fourth valves V1, V2, V3 and V4 are closed. The fourth and seventh valves V4 and V7 are opened from inlet to inlet. The fifth valve V5 is opened between the partial outlet and the left inlet. The sixth valve V6 is opened between the partial outlet and the right inlet. All pumps P1, P3 and P4 are off.

The diffusion module 37 is then flushed in method step 402. To this end, the first measuring pump P1 is switched on. The transport solution 36 flushes through the diffusion module 37 and any residues that may be present into the waste container 32.

The following method steps 403 to 406 relate to the measurement on the second measurement cell 35b and can take place in parallel or alternatively to the method steps 407 to 409, which relate to the measurement on the first measurement cell 35a.

In method step 407, the first measurement cell 35a is flushed in this way. For this purpose, the fourth valve V4 is opened between the partial outlet and the left inlet. Then (with the first measuring pump P1 still working) the transport solution 36 can be flushed through the first measurement cell 35a, with any residues that may be present being flushed into the waste container 32.

In method step 408, the first measurement cell 35a is calibrated. For this purpose, the first measuring pump P1 is first switched on, the fifth valve V5 is opened from the partial outlet to the left inlet, the fourth valve V4 is opened from the inlet to the inlet and the second valve V2 is opened from the partial outlet to the left inlet. A calibration measurement of the first calibration solution 33a in the first measurement cell 35a is carried out. Then, the second valve V2 is closed and the sample pump P3 is switched off.

Then one waits for a short time.

Then, the second valve V2 is opened from the partial outlet to the right inlet and the sample pump P3 is switched on, Now, the first calibration solution 33a can be pumped to the diffusion module 37 and/or the first measurement cell 35a. A further calibration measurement of the first calibration solution 33a is carried out in the first measurement cell 35a. Then, the second valve V2 is closed and the sample pump P3 is switched off.

In method step 409, a measurement is carried out on the first measurement cell 35a. For this purpose, the fifth valve V5 is opened from inlet to inlet, the fourth valve V4 is closed, the third valve V3 is opened from inlet to inlet, and a measuring loop is carried out in which:
  a) the first pump P1 is switched off.
  b) one waits for a predetermined diffusion period until components (e.g., the smaller molecules 103) of the medium 100 as the first sample have diffused through one of the two membranes 15 and 16 (in the exemplary embodiment shown in FIG. 2 through the second membrane 16).

c) then, the first measuring pump P1 is switched off again.

d) the first measuring pump P1 is switched on until the first sample thus taken is transported into the first measurement cell 35a. A measurement takes place in the first measurement cell 35a, in particular a determination of the concentration of the respective components of the medium 100 to be examined.

e) one waits again for a short time.

In parallel or as an alternative to these steps, the second measurement cell 35b is flushed in method step 403. For this purpose, the second measuring pump P2 is switched on, as a result of which the transport solution 36 is flushed through the valves V7 and V6 and through the second measurement cell 35b, with any residues that may be present being flushed into the waste container 32.

In method step 404, the adsorber for the solution buffer 39a is prepared. To this end, the second measuring pump is switched off, the sixth and first valves V6 and V1 are opened from the partial outlet to the left inlet, and the adsorber pump P4 is switched on. The solution buffer 39a is now pumped through the second measurement cell 35b.

In method step 405, a sample of the target protein 102 is taken in the sampling module 20. For this purpose, the fourth pump P4 is switched off, the sixth valve V6 is opened from the partial outlet to the right inlet, the first valve V1 is closed, and the second measuring pump P2 is switched on. Then, e.g., one can wait for a predetermined diffusion period until components (in particular proteins 102) of the medium 100 as a second sample have diffused through one of the two membranes 15 and 16 (in the exemplary embodiment shown in FIG. 2 through the first membrane 15).

The second measuring pump P2 is switched on again and a diffusion into the second measurement cell 35 is awaited. Then, the second measuring pump P2 is switched on again.

Method step 405 can run in several cycles.

In method step 406, a protein measurement is carried out on the second measurement cell 35b. First, the second measuring pump P2 is switched off.

This is followed by flushing, wherein the sixth valve V6 is opened from the inlet to the inlet, the seventh valve V7 is opened from the partial outlet to the left inlet, the first valve V1 is opened from the partial outlet to the right inlet, and the fourth pump P4 is switched on. The solution buffer 39b now displaces the binding buffer 39a. Both dilution and measurement take place in the second measurement cell 35b, wherein the sixth valve V6 is opened from the partial outlet to the left inlet. During the measurement in the second measurement cell 35b, in particular a concentration determination of the respective components of the medium 100 to be examined (here: the target protein 102) can take place.

The method is terminated with the last method step 410. Alternatively, the method can also be carried out iteratively, that is, instead, it can be continued again with method steps 400 or 301 etc.

The method steps highlighted in gray in FIGS. 6 and 7 are necessary method steps, while some or all of the method steps highlighted in white can be omitted or can only be carried out optionally.

REFERENCE NUMERAL LIST 10 extraction region
10a extraction region
10b extraction region
11 sample tip
12 common detection channel
12a first detection channel
12b second detection channel
13 common removal channel
13a first removal channel
13b second removal channel
14 transport line
15 first membrane
16 second membrane
17 intermediate region
20 sampling module
21 sterile connection
22 pump
30 analysis module
31 analyte sensor
32 waste container
33a first calibration solution
33b second calibration solution
34 inspection device
35a first measurement cell
35b second measurement cell
36 transport solution
37 diffusion module
38 membrane adsorber
39a binding buffer
39b solution buffer
100 medium
101 cell
102 protein/antibody
103 small molecule
200 bioreactor
201 RM bioreactor
F filter
P1 first measuring pump
P2 second measuring pump
P3 sample pump
P4 adsorber pump
V1 first valve
V2 second valve
V3 third valve
V4 fourth valve
V5 fifth valve
V6 sixth valve
V7 seventh valve
T transport direction

The invention claimed is:

1. A device for examining a medium inside a bioreactor comprising a sampling module for taking a sample of the medium, wherein:
   the sampling module comprises an extraction region disposed inside the bioreactor and contacting the medium,
   at least two different membranes for taking a sample of the medium are arranged at the extraction region of the sampling module,
   a first membrane of the at least two different membranes includes a first cutoff pore size of 50 kDa to 200 kDa,
   a second membrane of the at least two different membranes includes a second cutoff pore size of 10 kDa to 30 kDa, and
   the first membrane and the second membrane are arranged on an outer region of the extraction region so that the first membrane and the second membrane are disposed inside the bioreactor and contact the medium.

2. The device according to claim 1, wherein
the first membrane of the at least two different membranes is designed and arranged to allow proteins to pass from the medium into the sampling module contacting the medium, and
the second membrane of the at least two different membranes is designed and arranged to allow nutrients and/or metabolites to pass from the medium into the sampling module contacting the medium.

3. The device according to claim 1, wherein the sampling module has at least one transport line for transporting an adsorber through the extraction region along the transport line, and the first membrane and the second membrane of the at least two different membranes limit the transport line to the outside.

4. The device according to claim 3, with a control module for controlling an adsorber flow through the at least one transport line of the sampling module.

5. The device according to claim 3, wherein the sampling module has exactly one transport line through the extraction region, and the first membrane and the second membrane of the at least two different membranes are arranged one behind the other in the transport direction through the transport line.

6. The device according to claim 3, wherein the sampling module has at least two transport lines through the extraction region, and the first membrane and the second membrane of the at least two different membranes are arranged in different transport lines.

7. The device according to claim 1, wherein the first membrane and the second membrane of the at least two different membranes are designed as dialysis membranes or semipermeable membranes.

8. The device according to claim 1, further comprising an analysis module for examining a sample of the medium taken by the sampling module.

9. The device according to claim 8, wherein the analysis module is designed to determine a concentration of at least two different components in the medium by examining the sample of the medium taken.

10. A method for examining a medium inside a bioreactor, comprising:
arranging an extraction region of a sampling module within a bioreactor and in contact with the medium;
taking a sample of the medium through a first membrane and a second membrane of the extraction region, wherein the first membrane includes a first cutoff pore size of 50 kDa to 200 kDa, wherein the second membrane includes a second cutoff pore size of 10 kDa to 30 kDa, and wherein the first membrane and the second membrane are arranged on an outer region of the extraction region so that the first membrane and the second membrane are disposed inside the bioreactor and contact the medium; and
examining the sample of the medium taken.

11. The method according to claim 10, wherein the first membrane and the second membrane contact the medium in such a way that components of the medium pass through the first membrane and the second membrane and into at least one transport line extending through the extraction region of the sampling module.

12. The method according to claim 11, wherein an adsorber flow through the at least one transport line is controlled in such a way that the components of the medium pass through the first membrane and the second membrane and into an adsorber resting in the transport line for a predeterminable period of time before the enriched adsorber is transported to an analysis module disposed along the at least one transport line.

13. The method according to claim 10, wherein the sample of the medium has at least two components that are extracted separately from one another through the first membrane and the second membrane, and the at least two components are separated by an air bubble.

* * * * *